United States Patent [19]

Chiu et al.

[11] Patent Number: 4,886,678
[45] Date of Patent: Dec. 12, 1989

[54] METHOD FOR MANUFACTURE OF JELLY GUM CONFECTIONS

[75] Inventors: Chung-Wai Chiu, Westfield; James P. Zallie, Bound Brook, both of N.J.

[73] Assignee: National Starch and Chemical Corporation, Bridgewater, N.J.

[21] Appl. No.: 267,041

[22] Filed: Nov. 4, 1988

[51] Int. Cl.$^4$ .............................................. A23G 3/00
[52] U.S. Cl. .................................... 426/578; 426/660; 426/661; 426/658
[58] Field of Search ................ 426/660, 661, 658, 578

[56] References Cited

U.S. PATENT DOCUMENTS

| | | | |
|---|---|---|---|
| 3,218,177 | 11/1965 | Robinson et al. | 426/661 |
| 3,265,509 | 8/1966 | Wurzburg et al. | 426/661 |
| 3,446,628 | 5/1969 | Schoch et al. | 426/661 |
| 3,565,765 | 2/1971 | Heady et al. | 426/661 |
| 3,940,505 | 2/1976 | Nappen et al. | 426/661 |
| 3,974,032 | 8/1976 | Harjes et al. | 426/661 |
| 3,974,033 | 8/1976 | Harjes et al. | 426/661 |
| 3,974,034 | 8/1976 | Horn et al. | 426/661 |
| 4,225,627 | 9/1980 | Moore | 426/661 |
| 4,454,161 | 6/1984 | Okada et al. | 426/661 |
| 4,567,055 | 1/1986 | Moore | 426/661 |
| 4,726,957 | 2/1988 | Lacourse et al. | 426/661 |

OTHER PUBLICATIONS

Rutenberg, M. W., "Starch and Its Modifications", pp. 22–36 in *Handbook of Water-Soluble Gums and Resins*, R. L. Davidson, Editor, McGraw Hill, Inc., N.Y., N.Y. (1980).

Anon., *Bulletin-Leatherhead Food R. A.*, vol. 22, No. 6, Jun. 1988.

*Primary Examiner*—Jeanette Hunter
*Attorney, Agent, or Firm*—Mary E. Porter; Edwin M. Szala

[57] ABSTRACT

This invention provides a method for manufacture of jelly gum confections at lower temperatures utilizing conventional confectionery formulations containing starch which has been debranched by treatment with an endo-alpha-1,6-D-glucanohydrolase to provide lower hot viscosity and improved set time, processing conditions and gel quality. The method comprises the steps of blending the debranched starch with sweetener(s), water and other confectionery ingredients, heating the mixture to gelatinize the starch, and forming the confections. This invention also provides confections manufactured by this method.

11 Claims, No Drawings

METHOD FOR MANUFACTURE OF JELLY GUM CONFECTIONS

BACKGROUND OF THE INVENTION

This invention relates to an improved method for manufacture of jelly gum confections employing enzymatically debranched starches. This invention also relates to confections made by this method.

Jelly gum confections ("confections") are characterized by a translucent, resilient gel structure. These confections include gum drops, gum slices (sugared jellies), jujubes (hard gums), fruit gums (imitation fruit pieces) and jelly beans.

Starch is typically used to form the gel that is characteristic of these confections. In addition to a starch or starch blend, confection formulations include one or more sweeteners, water, flavoring, coloring and other confectionery ingredients.

These confections are manufactured by blending the ingredients, heating an aqueous dispersion of the starch, with or without the other ingredients, to the point where the starch becomes completely gelatinized, and molding or extruding the hot blend to form the confection pieces. The pieces may be coated with sugar, starch, oil or other ingredients to produce the finished confection.

For many years, these confections were molded by the starch cast mold method ("Mogul system"). In this method, the hot liquid confection is deposited into molds formed in a bed of dry starch. Disadvantages inherent in this method, such as long gel setting and drying times, high temperature heating requirements and starch cast mold handling problems, led to the development of alternative methods and formulations.

For example, U.S. Pat. No. 4,225,627 to Moore describes a starchless molding method which uses steam to release confection from their molds.

U.S. Pat. No. 3,265,509 to Wurzburg, et al. describes an extrusion process for manufacture of confections employing a high amylose starch.

U.S. Pat. No. 4,567,055 to Moore describes the development of extrusion processes for manufacture of confections and sets forth an improvement thereon.

Others have suggested modifications in the confection formulation to improve the process and the quality of the gel in the finished confection. U.S. Pat. No. 3,218,177 to Robinson, et al teaches the use of a starch consisting essentially of amylose and amylopectin in a ratio of 75:25 to 40:60. In using this type of starch, a starch slurry must be heated to at least 135° C., and preferably 140°–165° C., to obtain the complete starch gelatinization which is essential to the manufacture of an acceptable confection.

U.S. Pat. No. 3,446,628 to Schoch, et al teaches the use of a solvent-defatted, thin-boiling starch with a fluidity range of 30 to 80 and an amylose content not in excess of 35%. It is claimed that this starch sets quickly in to a gel and forms an acceptable confection after heating to 129°–135° C. for 26–28 seconds with a steam injection cooker. The disadvantage of this method is that the starch must be treated with a solvent to remove fat.

U.S. Pat. No. 4,726,957 to Lacourse, et al teaches the use of an acid-or enzyme-converted high amylose starch in these confections. Alphaamylase enzyme is employed for the enzyme conversion of the starch. This starch provides low hot viscosity and acceptable gel set time in addition to the desirable gel character of high amylose starch. However, a high temperature, pressurized cooking process is required to gelatinize the starch.

In spite of these attempts to improve traditional confection manufacturing, there remains a need for efficient methods which do not compromise confection quality.

It is well known that high amylose starches yield a more desirable gel strength and texture in these confections, particularly when the formulation contains a blend of the high amylose starch and a thin-boiling starch. However, the hot viscosity of the starch tends to increase to an undesirable level when high amylose starch is used, and high temperature cooking is required to gelatinize the starch.

Furthermore, high amylose starches are obtained from special hybrids of corn, barley and pea which contain as much as 70% amylose, and are more expensive and more difficult to isolate or handle than the starches from readily available sources such as corn, potato, wheat, rice, tapioca and the like. Most of the readily available starches contain less than 30% amylose.

Starch is a polysaccharide typically comprising a mixture of about 20–25% amylose and about 75–80% amylopectin which is organized into compact granular structures. Amylose is a linear polymer of D-anhydroglucose units which are linked by alpha-1,4-D-glucosidic bonds. Amylopectin is a large branched polymer of amylose chains linked by alpha-1,6-D-gluocosidic bonds in a tree-like structure. Depending upon the variety of plant from which the starch is obtained, amylose ordinarily contains between 250 and 12,500 D-anhydroglucose units and amylopectin contains between 400,00 and 3,125,000 D-anhydroglucose units.

In this invention, a starch containing a high percentage of short chain amylose (i.e., amylose of a molecular weight of no more than 20,000 measured against dextran standards by gel permeation chromatography) is produced from any of the readily available amylopectin-containing starches by treating the starch with an enzyme capable of cleaving the alpha-1,6-D-glucosidic linkages of the amylopectin. This enzymatic treatment cleaves the branch points in the amylopectin molecule, yielding a mixture of short chain amylose and partially debranched amylopectin, together with any remaining amylopectin or any long chain amylose present in the untreated starch.

In addition to providing functional properties similar to a high amylose starch (e.g., gel strength), this debranched starch mixture also improves the quality of the confection gel, provides low hot viscosity during processing, and required lower cooking temperatures than high amylose starch.

Thus, it is an object of this invention to provide jelly gum confections and a method of their manufacture employing starches which possess the desirable gel properties of a high amylose starch, but do not require high temperature cooking nor exhibit the high hot viscosity of high amylose starch. These properties are advantageously provided by a starch which has been enzymatically debranched.

SUMMARY OF THE INVENTION

This invention provides a method for manufacture of jelly gum confections employing a starch that has been debranched by treatment with an enzyme. This invention also relates to confections manufactured by this method. The enzymatic debranching process yields modified starch that is capable of gelling at a lower temperature than high amylose starch, yields confections of comparable gel strength to high amylose starch confections, but has lower hot viscosity than high amylose starch. The low hot viscosity permits deposition of liquid confections into molds at significantly higher solids (e.g., at about the solids of the finished confection). Drying times are thereby shortened. Additionally, the debranched starch produces a more acceptable gel texture and character in the confections of the invention and is more economical than high amylose starch.

The method of manufacturing these confections comprises the steps of: (1) enzymatically debranching the starch to provide a product capable of setting to a gel suitable for use in jelly gum confections; (2) blending the debranched starch into a suitable confectionery formulation; (3) heating the blend to the point where the starch is gelatinized and the solids are fully dispersed; and (4) forming the confection pieces.

Enzymes which may be employed in the first step of this method include pullulanase, isoamylase and any other endo-enzyme which hydrolyzes only the alpha-1,6-D-glucosidic linkages of starch. The product of the enzyme treatment is a starch comprising partially or fully debranched amylopectin and short chain amylose, together with any remaining amylopectin and any long chain amylose present in the starch prior to treatment. Starch preferred for use in this method contains up to 80% short chain amylose. This debranched starch may be blended with fluidity starch(es) in the confections of this invention.

The next step is to add the debranched starch or starch blend to any of the jelly gum confection formulations which are known in the art. Such formulations typically comprise 5 to 17% starch, 70 to 90% sweetener, and 0 to 20% confectionery ingredients (such as flavorants, colorants, fats, oils, humectants, vitamins, preservatives and mixtures thereof), on a dry weight basis. The amount of water employed depends on the type of starch and sweetener, the type of cooking process, the type of forming process and other variables which may be selected and controlled by the practitioner. The amount of water typically ranges from 10-30%, by weight, of the total formulation.

The confectionery formulation must be cooked to gelatinize the starch and fully disperse the solids. Unlike high amylose starch-containing confections which are typically gelatinized at greater than atmospheric pressures and temperatures of at least 330° F. (165° C.), the debranched starch confections herein only require jet-cooking for a few seconds at about 265° F. (130° C.) or atmospheric cooking at 190°–240° F. (93°–115° C.) to achieve gelatinization of starch blends and full dispersion of solids.

The remaining steps necessary to complete the manufacture of jelly gum confections which are known to the practitioner and include molding the cooked formulation, and tempering, drying and finishing the confection pieces. When this method is used for manufacture of confections, the low hot viscosity of the debranched starch formulation permits easier handling during molding.

Additionally, the rapid set time of the debranched starch formulation permits more rapid drying and finishing of the confection pieces.

The jelly gum confections of this invention compare favorably to those of a high amylose starch formulation in gel strength. Moreover, they exhibit improved clarity, smoother texture and better shelf-life characteristics when compared with high amylose starch confections.

DESCRIPTION OF THE PREFERRED EMBODIMENTS

The starches which may be employed in preparation of the debranched starches useful herein may be derived from any source including corn, potato, sweet potato, wheat, rice, sago, tapioca, waxy maize, sorghum, and the like. Starches or blends of starches which contain less than 65% amylose are preferred.

The starches may also be converted for use in certain confection formulations. Suitable conversion of the starches to thin-boiling or fluidity starches useful herein may be achieved by standard oxidative, heat, acid or alpha-amylase enzyme conversion techniques. A method for starch conversion employing alpha-amylase is disclosed in U.S. Pat. No. 4,726,957 to Lacourse, et al. Other conversion techniques are well known in the art. See, M. W. Rutenburg, "Starch and Its Modifications" in *Handbook of Water-Soluble Gums and Resins*, R. L. Davidson, editor, McGraw Hill, Inc., New York, New York, 1980, pp 22–36.

In a preferred embodiment, the next step after starch conversion is starch gelatinization. The gelatinization process disrupts, in whole or in part, the associative bonding of the starch molecules within the raw starch granule, thereby making the molecules more accessible to the enzyme and permitting the enzyme to more easily and uniformly debranch the starch molecules. After a slurry of the starch has been gelatinized, the solids, temperature and pH of the starch dispersion are adjusted to provide optimum enzyme activity.

The optimum parameters for enzyme activity will vary depending upon the enzyme used. The rate of starch debranching will depend on factors including enzyme concentration, substrate concentration, pH, temperature, the presence or absence of inhibitors and other factors. Depending on the type of enzyme, or its source, various parameters may require adjustment to achieve optimum debranching rate. In general, the enzymatic debranching is carried out at the highest feasible solids content to facilitate subsequent drying of the starch while maintaining optimum debranching rate. For example, for the pullulanase, used herein, a precooked starch dispersion ranging up to 28% is preferred.

The practitioner will recognize that a higher solids system (e.g., above 50% solids) may be employed if the starch is gelatinized with a process which produces adequate mixing to blend the starch and the enzyme at higher solids. The practitioner will also recognize that the temperature, treatment time, and other parameters of the enzymatic debranching process must be adjusted to the higher solids content. Processes which employ higher solids starch dispersions are intended to fall with the scope of this invention and may be used to prepare the modified starch herein.

Although the debranching is illustrated employing pullulanase (E. C. 3.2.1.41, pullulan 6-glucanohydrolase), other endo-alpha-1,6-D-glucanohydrolases, such as isoamylase (E.C. 3.2. 1.68), or any other endoenzyme which exhibits selectivity in cleaving the 1,6-linkages of the starch molecule but leaving the 1,4-linkages substantially intact, may be used to prepare the modified starch herein.

In a preferred embodiment, the enzyme is a heat-stable debranching enzyme obtained from a novel species of Bacillus. It belongs to the group of debranching enzymes known as pullulanases. It catalyses the hydrolysis of the alpha-1,6- linkages in pullulan and amylopectin, provided that there are at least two glucose units in the side chain. Pullulan is a linear polymer consisting essentially of alpha-1,4-D-glucopyranosyl triose units joined by alpha-1,6-linkages. Amylopectin and amylose are the two polymers present in starch. Unlike amylose, which is a linear polymer of alpha-1,4-linked glucopyranosyl units, amylopectin is a branched polymer of glycopyranosyl units, containing alpha-1,6-D-glucosidic bonds in addition to alpha-1,4-linkages.

Optimum concentrations of enzyme and substrate are governed by the level of enzyme activity. Enzyme activity is determined by the source and type of enzyme and the concentration of enzyme in commercially available batches.

Although the debranching is carried out using an enzyme in solution, processes utilizing an enzyme immobilized on a solid support are intended to fall within the scope of this invention.

The reaction may proceed in the presence of buffers to ensure that the pH will be at the optimum level throughout the degradation. Buffers such as acetates, citrates, or the salts of other weak acids are acceptable. Other agents may be used to optimize enzyme activity. The reaction may be carried out in a pH range from about 3.0 to 7.5, with the preferred range being between 4.5 and 5.5 and the optimum being 5.0 at 60° C. for the pullulanase obtained from Bacillus and utilized herein.

The aqueous starch dispersion should be held during the enzymatic digestion at a temperature of about 25°-100° C., the preferred range for Bacillus pullulanase being 55°-65° C. and the optimum being 60° C. at pH 5.0. However, if shorter reaction times are desired, a temperature range from 60°-65° C. or a higher enzyme concentration may be used. Alternatively, a higher temperature may be employed if a thermally stable debranching enzyme which yields short chain amylose from starch is selected for use herein. As with other parameters of the enzyme treatment, the preferred and optimum temperature ranges will vary with changes in other parameters such as substrate concentration, pH and other factors affecting enzyme activity, and can be determined by the practitioner.

The enzyme reaction is permitted to continue until the desired level of debranching is reached. The progress of enzyme reaction may be measured by various methods. If all critical parameters have been established for achieving a particular starch composition, then the reaction may be allowed to proceed to a predetermined relative end point in time. The end point also may be monitored and defined by measuring the concentration of reducing sugars. The reducing groups which are freed by 1,6-D-alpha-glucanohydrolase activity are measured by methods well known in the art. Other techniques such as monitoring the change in viscosity, iodine reaction, or the change in molecular weight may also be used to define the reaction end point.

In a preferred embodiment, the debranching end point is measured by determining the funnel viscosity of the starch dispersion, or, for corn starch and other starches containing long chain amylose, the caustic funnel viscosity of the starch dispersion.

In a second preferred embodiment, the degree of starch debranching is measured by gel permeation chromatography. After separating the starch into its different molecular weight fractions, the percentage of short chain amylose is determined by calculating the percentage, by weight, of the low molecular weight fraction of the partially debranched starch. It will be understood by the practitioner that these percentages are approximately equal to the amount of short chain amylose which has been liberated from the amylopectin by the debranching enzyme. Experimental error in gel permeation chromatography (e.g., due to contamination by the enzyme, or by sugars or dextrins introduced with the starch, the enzyme solution, the buffer or other process components) may result in a low molecular weight fraction which may range up to 5% more than the percent short chain amylose in the starch sample.

The degree of starch debranching needed for jelly gum confections depends on the type of starch utilized and the degree, if any, of conversion. Slight improvements in gel strength and hot viscosity are observed with corn starch containing as little as 5% short chain amylose. Fully debranched corn starch (essentially amylopectin-free) may be employed alone or in starch blends with a fluidity starch. Fully debranched waxy maize starch may be employed in starch blends with a fluidity starch. Debranched corn or waxy maize starches comprising from 15 to 65% short chain amylose are preferred.

After the desired degree of starch debranching has been reached, the enzyme may be deactivated. Pullulanase is rapidly deactivated at temperatures above about 70° C., therefore, the reaction may be conveniently terminated by increasing the temperature of the starch dispersion to at least 75° C. for about 15 minutes.

If the confection requires purification of the debranched starch composition, the reaction impurities and by-products may be removed by dialysis, filtration, centrifugation or any other method known in the art for isolating and concentrating starch compositions.

If a dried starch composition is desired, the starch may be dried by any method known in the art.

Blends of starches which contain at least 5% of the enzymatically debranched starch may be used in the confections. The blends preferably contain less than 80%, and most preferably 30–75%, of converted starch in order to provide the confection with lower hot flow viscosity in addition to gel strength. For starches which are blended with the debranched starch, oxidative, heat or acid conversion is preferred due to the ease in handling and recovery by granular starch, as opposed to the dispersed form of starch used in alpha-amylase conversion.

Converted, or thin-boiling confectioner's cooking starches which include acid-hydrolyzed or oxidized corn, sorghum, and wheat starches having amylose contents of 25–35% are preferably employed in the blend, with acid-hydrolyzed corn starch being most preferred.

The sweetener component of confection formulations may include a wide array of sweeteners and sweetening agents. Typical sweetening compositions include, for example, combinations of sucrose, dextrose, fructose, maltodextrin, corn syrup, hydrogenated corn syrup, and invert syrup. Other nutritive lower and higher saccharides as well as nonnutritive sweeteners (e.g., aspartame, saccharin, etc.) may also be employed.

The confections herein may also advantageously contain various other optional confectionery ingredients including, for example, natural flavorants (preferably fruit) and artificial flavorants, fats, oils, surfactants, humectants, vitamins, preservatives, and mixtures thereof.

The natural fruit flavorants useful in the present composition may include fruit purees and fruit puree concentrates which have a high moisture content. One may also advantageously employ dehydrated fruit solids in the preparation of the confections. The dehydrated solids may consist entirely of fruit. We preferably employ dried fruit solids prepared according to the procedure described in U.S. Pat. No. 3,940,505 to Nappen, et al, where the fruit is drum dried in the presence of a suitable amount of a granular or pregelatinized starch. The disclosure of U.S. Pat. No. 3,940,505 is hereby incorporated by reference.

Formulations having confection gel strengths after setting which are similar to those of comparable high amylose starch-containing formulations, and higher than those of commonly used fluidity starches (e.g., 67WF cornstarch) are preferred. It should be recognized by those skilled in the art that, in addition to the type and amount of starch employed in the formulation, the amount and composition of any optional confectionery ingredients employed will have an effect on the ultimate gel strength of the confection.

Confectionery formulations useful herein include numerous embodiments which are well known in the art. The jelly gum confections herein preferably comprise, on a dry substance basis, from about 5–17% of the starch blend, about 70–95% sweetener solids and about 0–20% of one or more of the confectionery ingredients described above. The method of preparation of the confections may be achieved by one of many conventional means. Typically, a two stage preparation technique is employed. In the first stage, the starch component and a portion or all of the sweetener component are homogenously dissolved in a suitable amount of water. The dissolution may be achieved by retort or jet cooking the starch or starch blend in the presence of a portion or all of the sweetener component. The slurry is cooked for an amount of time sufficient to gelatinize the starch. In a preferred embodiment, the starch is jet cooked at 130° C. for a few seconds. The total amount of water necessary for dissolution will typically range from about 10–30% of the total formulation.

In the second stage of preparation, any remaining sweetener as well as all additional confectionery ingredients are added to the dispersed slurry. Prior to deposition in molds, the confection is concentrated, if desired, to a concentration preferably ranging between 72–85% solids.

The following examples will more fully illustrate the embodiments of this invention. In the examples, all parts and percentages are given by weight and all temperatures are in degrees Celsius, unless otherwise noted.

The following test procedures were used to characterize the starches useful herein and the confections produced therewith.

SOLUBLE SOLIDS

The percent soluble solids was measured with an Abbe refractometer.

HOT FLOW VISCOSITY

The hot flow viscosity of the composition was measured by the Ford Cup viscosity method using 35 ml samples at 190°–200° F. (87°–93° C.). A standardized Ford cup fitted with a #4 orifice was employed. The Ford cup viscosity is the time (in seconds) required for 35 ml of a confection sample at a temperature of 190°–200° F. (87°–93° C.) to flow through the orifice. The thinner (i.e., lower) the viscosity of the confection, the faster it will flow. In order to ensure that the confection does not gel in the cup during evaluation, the cup is preheated to a temperature of about 80° C. prior to evaluation.

GEL STRENGTH

Gel strength of the confections was measured with a Stevens LFRA Texture Analyzer employing ball probe #7, run at a speed of 0.5 mm./sec. The force (in grams) required to penetrate the confection a distance of 4 mm with the #7 probe is measured three times and the average of the three measurements recorded. Gel strength measures are susceptable to some experimental error arising from batch-to-batch variation in the moisture content of the steam used to cook the confection, or the atmospheric temperature and humidity during confection cooling and setting, or the time lapse between blending the starch and cooking, or other variations which will be apparent to the practitioner.

WATER FLUIDITY

The water fluidity of the blending starches is measured using a Thomas Rotational Shear-Type Viscometer (manufactured by Arthur H. Thomas Co., Philadelphia, PA 19106), standardized at 30° C. with a standard oil having a viscosity of 24.73 cps., which oil requires 22.08+0.05 sec for 100 revolutions. Accurate and reproducible measurements of the water fluidity are obtained by determining the time which elapses for 100 revolutions at different solids levels depending on the starch's degree of conversion (as conversion increases, the viscosity decreases). The procedure used involves slurrying the required amount of starch (e.g., 6.16 g dry basis) in 100 ml of distilled water in a covered copper cup and heating the slurry in a boiling water bath for 30 min with occasional stirring. The starch dispersion is then brought to the final weight (e.g., 107 g) with distilled water. The time required for 100 revolutions of the resultant dispersion at 81°–83° C. is recorded and converted to a water fluidity number as defined in the table below.

| Time Required for 100 Revolutions (seconds) Amount of Starch Used (anhydrous, g) | | | | |
|---|---|---|---|---|
| 6.16[a] | 8.80[b] | 11.44[c] | 13.20[d] | Water Fluidity |
| 60.0 | | | | 5 |
| 39.6 | | | | 10 |
| 29.3 | | | | 15 |
| 22.6 | | | | 20 |
| 20.2 | | | | 25 |
| | 33.4 | | | 30 |
| | 27.4 | | | 35 |
| | 22.5 | | | 40 |
| | | 32.5 | | 45 |
| | | 26.8 | | 50 |
| | | 22.0 | | 55 |
| | | | 24.2 | 60 |
| | | | 19.2 | 65 |
| | | | 15.9 | 70 |

-continued

| Time Required for 100 Revolutions (seconds) Amount of Starch Used (anhydrous, g) | | | | Water Fluidity |
|---|---|---|---|---|
| 6.16[a] | 8.80[b] | 11.44[c] | 13.20[d] | |
| | | | 13.5 | 75 |
| | | | 11.5 | 80 |
| | | | 10.0 | 85 |
| | | | 9.0 | 90 |

For a, b, c, and d, final weights of starch solutions are 107, 110, 113, and 115 g, respectively.

FUNNEL VISCOSITY

The viscosity of the enzymatically debranched starches was also measured using the funnel viscosity method.

To measure funnel viscosity at 19% solids, 38 g of the starch (anhydrous basis) was weighed into a tared 250 ml beaker (stainless steel) containing a thermometer and brought to 200 g total weight with distilled water. The sample was mixed to dissolve any lumps and heated or cooled to 72° F. (22° C.) A total of 100 ml of the starch dispersion was measured into a graduated cylinder. It was then poured into a calibrated funnel while using a finger to close the orifice. A small amount was allowed to flow into the graduate to remove any trapped air, and the complete balance remaining in the graduate was poured back into the funnel. Using a timer, the time required for the 100 ml sample to flow through the apex of the funnel was recorded.

The funnel was a standard 58°, thick-wall, resistance glass funnel whose top diameter was about 9–10 cm with the inside diameter of the stem being about 0.381 cm. The funnel was calibrated so as to allow 100 ml of water to go through in 6 seconds using the above procedure.

CORN STARCH FUNNEL VISCOSITY

Due to retrogration of the starch which occurs when using corn starch, the funnel viscosity measurement was modified as follows for debranched corn starch: 1. the starch sample weight was reduced to 15 g (anhydrous basis); 2. sufficient hot (at least 90° C.) water was added to the starch to bring to 150 g total weight; 3. 15 g of 25% w/v sodium hydroxide solution was added to the hot starch slurry; and 4. with stirring, the slurry was cooled to 72° F. and the measurement carried out as set forth above.

GEL PERMEATION CHROMATOGRAPHY

Starches were prepared for analysis by slurrying 5 mg of starch in 4 ml of dimethylsulfoxide ("DMSO") containing 0.03M sodium nitrate and heating the slurry to 80° C. for at least 30 minutes. Samples (200 ul) were injected into an ALC/GPC-150C Chromatograph (Waters Associates, Milford, Massachusetts) (equipped with a Nelson 3000 Series Chromatography Data System and two PLgel mixed 10 um columns (obtained from Polymer Laboratory, Amherst, Massachusetts), employing DMSO containing 0.03M sodium nitrate as the mobile phase), and eluted at a rate of 1 ml/min. The column was calibrated using dextran standards (with molecular weights of 2,000; 20,000; 80,000; and 500,000, obtained from Pharmacia Fine Chemicals, Piscataway, New Jersey). The percentage short chain amylose was calculated from the relative area of the peak obtained within the molecular weight range from about 500 to 20,000.

EXAMPLE 1

This example describes the preparation of the debranched starches.

The starches were converted, where applicable, prior to gelatinization and treatment with pullulanase. To convert the starch, a slurry of 100 parts of starch in 150 parts of water was heated to 52° C., the indicated amount of hydrochloric acid (1.75%) was added, and the mixture was stirred for 16 hours at 52° C. The hydrolysis was stopped by neutralizing the mixture with alkali (a solution of 3% sodium hydroxide) to a pH of 5.5. The converted starch was recovered by filtration, washed and dried.

An aqueous slurry (20–30%) solids was prepared employing one of these converted starches, or where applicable, an unmodified starch. The aqueous starch slurry was jet-cooked at approximately 300° F. (149° C.) to gelatinize the starch. The cooked starch dispersion was placed in a constant temperature bath at 58°–60° C. with constant stirring. The pH was adjusted to 5 with 3% hydrochloric acid.

Depending on the type of starch used and its amylopectin content, between 0.5 and 10.0 mls of pullulanase per 100 g of starch were added to the cooked starch dispersion. The pullulanase (E.C. 3.2.1 41, pullulan 6-glucanohydrolase) which was used is a starch debranching enzyme produced by a novel species of Bacillus. This enzyme (Promozyme TM) was obtained from Novo Industri A/S of Denmark. The enzymatic activity of Promozyme in a 1.25 g/ml solution is standardized at 200 PUN/ml of solution. One PUN (Pullulanase Unit Novo) is the amount of enzyme which, under standard conditions, hydrolyses pullulan, liberating reducing carbohydrate with a reducing power equivalent to 1 micro-mol glucose per minute. The procedure for determining PUN is available from Novo Industri A/S.

Thus, in the starch dispersion employing cornstarch, 125 PUN of pullulanase per 100 g cornstarch was added to the dispersion. For the waxy maize starch slurry (with higher amylopectin content), 750 PUN of pullulanase per 100 g waxy maize starch was added to the dispersion.

The pullulanase was permitted to debranch the starch until the funnel viscosity of the starch slurry had fallen into the desired range (e.g., 14.8 seconds for corn starch containing 32.5% short chain amylose, as measured by gel permeation chromatography). The pullulanase was deactivated by heating the slurry to at least 80° C. The starch was spray-dried at an inlet temperature of 200°–210° C. and an outlet temperature of 85°–90° C. The spray-dried starch product was screened through #40 mesh screen.

EXAMPLE 2

This example illustrates that debranched starch may be successfully used in a commercial jelly gum confection formulation.

A formulation containing a corn starch which had been debranched to a caustic funnel viscosity of 14.8 seconds (10% solids) and contained 32.5% short chain amylose, was compared to a formulation containing a commercially used high amylose starch. The debranched starch was prepared by the method of Example 1. A corn starch containing 50% amylose (Hylon V) which is presently being commercially used in these confections was used in a control formulation.

The following jelly gum formation was used:

| Ingredient | % Weight | % Dry Solids |
|---|---|---|
| 62 DE Corn Syrup | 46.4 | 48.7 |
| Sugar | 29.4 | 37.7 |
| Starch [Total] | [11.6] | [13.6] |
| 30% Debranched or Hylon | 3.4 | 4.1 |
| 70% Blending | 8.2 | 9.5 |
| Water | 13.6 | 0.0 |
|  | 100.0 | 100.0 |

The blending starch (approximately 70% of the total starch blend) was a fluidity corn starch (67 WF) which is commonly used in such formulations to provide an acceptable hot flow viscosity and adequate gel structure. A control containing 100% of the 67 WF fluidity corn starch (the blending starch) was also prepared.

The jelly gum confection compositions were prepared by:

(1) heating the corn syrup until thin;
(2) adding the sugar and heating to 130°–150° F.;
(3) thoroughly blending the starch with the sweeteners;
(4) thoroughly blending hot water with the mixture of starch and sweeteners; and
(5) flash heating the mixture to 285° F. (140° C.) in a jet cooker.

The percentage soluble solids was determined just prior to jet cooking. The hot flow viscosity was determined just after jet cooking. The cooked composition was poured into 100 ml glass jars which were capped loosely until cool. After these samples had cooled to room temperature, any condensate was wiped from the caps and the jars were tightly sealed. Gel strength measurements were taken after 24 hours and after three weeks.

Results are summarized in Table I. Because the Hylon V starch was not fully dispersed after heating to 285° F. (140° C.), a second, fully dispersed sample was prepared by heating the formulation to 335° F. (168° C.).

TABLE I

| Sample | Hot Viscosity (seconds) | Gel Strength 24 Hours | 3 Weeks |
|---|---|---|---|
| Debranched[b] Corn Starch (30/70 blend)[a] (285° F.) | 47 | 273 | 444 |
|  | 444 |  |  |
| Hylon V (285° F.) (30/70 blend)[a] | 150 | 124 | 535 |
| Hylon V (335° F.) (30/70 blend)[a] | 49 | 288 | 411 |
| Fluidity (67 WF) Corn Starch (285° F.) | 65 | 139 | 452 |

[a]Total starch blend contains 70% of an acid-converted cornstarch (67 WF).
[b]Debranched to 14.8 second funnel viscosity.

The debranched starch had gel strength and stability comparable to the high amylose starch control which required cooking to a higher temperature (335° F.) for dispersion. In addition, the hot viscosity of the debranched starch was lower than that of the high amylose starch was cooked at the same temperature (285° F.). Thus, the debranched starch may be effectively used to replace high amylose starch in a jet-cooked process for preparing jelly gum confections.

EXAMPLE 3

In this example, the jet cook procedure and the confection formulation of Example 2 were employed to compare a variety of debranched starches prepared from different native starches and converted starches.

All starches, except the control and Hylon VII, were enzymatically debranched by the method set forth in Example 1. The Hylon VII starch (corn starch containing 70% long chain amylose) was debranched by the method of Example 1 except than an 8% solids slurry was jet-cooked, treated with 3 mls of enzyme per 100 g of starch for 6 hours, jet-cooked a second time and then spray-dried. The lower solids and second cooking step were needed to overcome the tendency of Hylon VII to retrograde. The debranched Hylon VII contained 17% short chain amylose. The other starches are described in Table II.

All debranched starches were blended with a 67 WF fluidity corn starch (30:70 ratio of debranched: fluidity starch) as in Example 2. Results are summarized in Table II.

TABLE II

| Sample* | Hot Viscosity (seconds) | Gel Strength 24 Hours | 3 Weeks |
|---|---|---|---|
| A Corn Starch Debranched to 26.8 sec. | 40.5 | 212 | 441 |
| B Fluidity (60 WF) Corn Starch Debranched to 15 sec. | 29.2 | 228 | 443 |
| C Waxy Maize Starch Debranched to 27 sec. | 27.8 | 175 | 401 |
| D Fluidity (50 WF) Waxy Maize Starch Debranched to 15 sec. | 21.0 | 203 | 373 |
| E Waxy Maize Starch Debranched to 15 sec. | 22.0 | 203 | 389 |
| F Waxy Maize Starch Debranched to 9.7 sec. | 18.7 | 202 | 333 |
| G Fluidity (67 WF) Corn Starch Control | 65.0 | 139 | 452 |
| H Hylon VII Debranched to 17% Short Chain Amylose | 54.6 | 348 | 456** |

*Debranched starches are used in a 30:70 blend with an acid-converted cornstarch (67 WF) which is widely used in jelly gum confections.
**Gel strength measured at 2 weeks.

The 24 hour gel strengths of debranched waxy maize and corn starches were greater than those of the fluidity corn starch control or the 285° F. cook, high amylose starch of Example 2. The hot viscosities were lower. Thus, a variety of debranched native and converted starches may be used to produce an acceptable jelly gum composition employing a cooking temperature of only 285° F.

EXAMPLE 4

This example illustrates the effects of employing different percentages of debranched starch in the starch blends used in the confection formulation of Example 2.

The formulation and procedure of Example 2 were used to prepare jelly gum confections from the starch blends described in Table III. Results of the confection evaluations are shown in Table III.

TABLE III

| Starch Blend Percent Composition | Hot Viscosity (seconds) | Gel Strength 24 Hours | Gel Strength 3 Weeks |
|---|---|---|---|
| A. 100% fluidity[b] | 65.0 | 139 | 452 |
| B. 5% debranched[a]: 95% fluidity[b] | 54.5 | 151 | 437[c] |
| C. 30% debranched[a]: 70% fluidity[b] | 26.1 | 229 | 389 |
| D. 40% debranched[a]: 60% fluidity[b] | 32.7 | 281 | 401 |
| E. 50% debranched[a]: 50% fluidity[b] | 19.1 | 259 | 321 |
| F. 100% debranched[a] | 18.5 | 175 | 211 |

[a]Corn starch debranched to 14.8 seconds.
[b]Corn starch acid-converted to 67 WF
[c]Gel strength measured after 4 weeks.

These results show that the best jelly gum confections are prepared from formulations containing starch blends of debranched and fluidity starches in ratios of 30:70 to 50:50. An improvement in hot viscosity is observed with blends containing as little as 5% debranched starch.

EXAMPLE 5

This example illustrates that fully debranched starch may be employed in the confection formulation of Example 2, however, gel strength is inferior to that obtained with partially debranched starch. The formulation and procedure of Example 2 were used to prepare jelly gum confections from the starch blends described in Table IV. Results of the evaluation are shown in Table IV.

TABLE IV

| Sample | Hot Viscosity (seconds) | Gel Strength 24 hours | Gel Strength 3 weeks |
|---|---|---|---|
| A. 100% fluidity starch[a] | 61.0 | 132 | 460 |
| B. 30/70 fully debranched waxy maize[b]/fluidity starch[a] | 17.0 | 146 | 287 |
| C. 100% fully debranched waxy maize starch[b] | 11.0 | 63 | 80 |
| D. 30/70 partially debranched waxy maize[c]/fluidity starch[a] (See Example 3) | 22.0 | 203 | 389 |

[a]Corn starch acid-converted to 67 WF
[b]Debranched to a funnel viscosity of 6.7 seconds at 19% solids.
[c]Debranched to a funnel viscosity of 15 seconds at 19% solids.

EXAMPLE 6

This example illustrates that formulations and procedures other than those of Example 2 may be employed in the manufacturer of jelly gum confections from debranched starches.

Jelly gum confections containing different blends of the debranched and fluidity starches of Example 4 were prepared from the following formulation:

| Ingredient | % Weight | % Dry Solids |
|---|---|---|
| 62 DE Corn Syrup | 29.8 | 49.2 |
| Sugar | 18.9 | 38.2 |
| Starch Blend | 7.4 | 13.6 |
| Water | 43.9 | — |
| | 100.0 | 100.0 |

KETTLE COOKING PREPARATION

The jelly gum confections were prepared by:
(1) preheating the water in a cooking kettle to 130° F. (54° C.);
(2) dry blending starches and sugar;
(3) adding dry blend to the water while mixing;
(4) boiling kettle contents for 10 minutes with intermittant stirring;
(5) adding hot corn syrup (150° F.) (66° C.) to kettle; and
(6) boiling kettle contents until desired percentage solids (73-75%) was reached.

Samples were placed into containers, stored and tested as set forth in Example 2. The starch blends tested are listed in Table V. Results are summarized in Table V. Starch samples containing up to 100% debranched corn starch produced low hot viscosity and acceptable gel strength and stability in an atmospherically cooked confection formulation.

TABLE V

| Sample | Hot Viscosity (seconds) | Gel Strength 24 Hours | Gel Strength 3 Weeks |
|---|---|---|---|
| A. 100% fluidity[b] | 106.5 | 127 | 459 |
| B. 30:70 debranched[a]/fluidity[b] | 36.9 | 265 | 385 |
| C. 50:50 debranched[a]/fluidity[b] | 24.3 | 297 | 421 |
| D. 100% debranched[a] | 10.7 | 268 | 305 |
| E. Hylon VII[c] | 56.7 | 323 | 411 |

[a]Corn starch debranched to 14.8 seconds (at 10% solids).
[b]Corn starch acid-converted to 67 WF
[c]High amylose (70%) corn starch debranched to contain 17% short chain amylose These examples illustrate that a starch which has been debranched by treatment with pullulanase exhibits desirable low hot viscosity and acceptable gel strength, quality and stability in jelly gum confections. In addition, the use of such debranched starches yields improved confection set time when compared with commercially used fluidity starch.

Now that the preferred embodiments of the present invention have been described in detail, various modifications and improvements thereon will become readily apparent to those skilled in the art. Accordingly, the spirit and scope of the invention are to be limited only by the appended claims, and not by the foregoing specification.

We claim:

1. A method for manufacturing jelly gum confections, comprising the steps of:
    (a) providing a starch which has been debranched by treatment with a debranching enzyme, which debranched starch comprises partially or fully debranched amylopectin and at least 5%, by weight, short chain amylose, said starch being capable of setting to a gel suitable for use in jelly gum confections;

(b) blending a confectionery formulation, comprising a sweetener, the starch and water;

(c) heating the blended formulation to a sufficient degree to gelatinize the starch and fully disperse the solids; and (d) forming jelly gum confections from the heated formulation;

wherein confection gel characteristics similar to those provided by high amylose starch are achieved at lower hot viscosities and at lower cooking temperatures than those required for high amylose starch.

2. The method of claim 1, wherein the debranched starch comprises up to 80%, by weight, short chain amylose and at least 20%, by weight partially debranched amylopectin.

3. The method of claim 1, wherein the debranched starch further comprises long chain amylose, amylopectin, or a combination thereof.

4. The method of claim 1, wherein the starch is provided by a method of debranching, comprising the steps of:

(a) gelatinizing the starch; and (b) debranching the starch by treatment with an endo-enzyme capable of hydrolyzing the alpha-1,6-D-glucosidic linkages of the starch.

5. The method of claim 4, wherein the enzyme is an endo-alpha-1,6-D-glucanohydrolase, selected from the group consisting essentially of pullulanase and isoamylase.

6. The method of claim 4, wherein the debranching is carried out with pullulanase at a pH of 5.0 and a temperature of 60° C.

7. The method of claim 1, wherein the starch is converted by treatment with acid, heat, oxidizing agents or alpha-amylase.

8. The method of claim 1, wherein the confectionery formulation comprises, on a dry weight basis, from 70 to 95% of at least one sweetener, 5 to 17% of the debranched starch, or a starch blend containing the debranched starch, and 0 to 20% of a confectionery item, wherein the confectionery item is a flavorant, colorant, fat, oil, surfactant, humectant, vitamin, preservative or mixture thereof.

9. The method of claim 8, wherein the starch blend comprises from 5 to 100% of the debranched starch and from 0 to 95% of a second starch, which second starch is corn, wheat, rice or sago.

10. The method of claim 9, wherein at least one of the starches is converted by treatment with acid, heat, oxidizing agents or alpha-amylase enzyme.

11. Jelly gum confections manufactured by a process comprising the steps of:

(a) providing a starch which has been debranched by treatment with a debranching enzyme, which debranched starch comprises partially or fully debranched amylopectin and at least 5%, by weight, short chain amylose, said starch being capable of setting to a gel suitable for use in jelly gum confections;

(b) blending a confectionery formulation, comprising a sweetener, the starch and water;

(c) heating the blended formulation to a sufficient degree to completely gelatinize the starch and fully disperse the solids; and (d) forming jelly gum confections from the heated formulation; wherein confection gel characteristics similar to those provided by high amylose starch are achieved at lower hot viscosities and at lower cooking temperatures than those required for high amylose starch.

* * * * *